United States Patent [19]

Hirschberg et al.

[11] Patent Number: 5,433,732
[45] Date of Patent: Jul. 18, 1995

[54] DEFIBRILLATOR WITH CURRENT LIMITER

[75] Inventors: Jakub Hirschberg, Taeby; Hans Strandberg, Sundbyberg, both of Sweden

[73] Assignee: Pacesetter AB, Solna, Sweden

[21] Appl. No.: 265,632

[22] Filed: Jun. 24, 1994

Related U.S. Application Data

[63] Continuation of Ser. No. 45,299, Apr. 12, 1993, abandoned.

[30] Foreign Application Priority Data

May 12, 1992 [EP] European Pat. Off. ............ 92107996

[51] Int. Cl.⁶ ............................................. A61N 1/36
[52] U.S. Cl. ............................... 607/7; 128/908
[58] Field of Search ............................ 607/5–8, 607/14; 128/640

[56] References Cited

U.S. PATENT DOCUMENTS

| | | | |
|---|---|---|---|
| 3,900,432 | 8/1975 | Marcus et al. | 252/219 |
| 4,466,295 | 5/1984 | Shibuta et al. | 528/168 |
| 4,745,923 | 5/1988 | Winstrom | 128/908 |
| 5,040,533 | 8/1991 | Fearnot | 607/36 |
| 5,275,157 | 1/1994 | Morgan et al. | 607/6 |
| 5,284,135 | 2/1994 | Lopin | 607/150 |
| 5,295,482 | 3/1994 | Clare et al. | 128/639 |

Primary Examiner—William E. Kamm
Assistant Examiner—Marianne Parker
Attorney, Agent, or Firm—Hill, Steadman & Simpson

[57] ABSTRACT

An implantable defibrillator has a charging circuit which charges a capacitance, electrodes for delivering energy from the capacitance to a heart, and a switching stage for discharging the capacitance through the electrodes and across heart tissue to defibrillate the heart, as needed. A non-inductive current limiter is connected in vivo in the discharge path for limiting the current supplied to the heart tissue to predetermined maximum value.

12 Claims, 1 Drawing Sheet

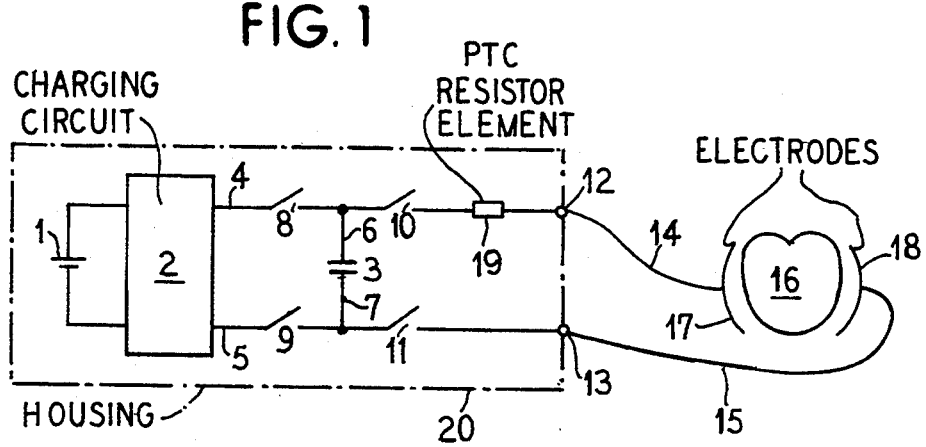
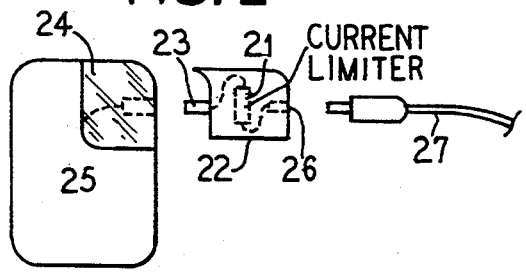
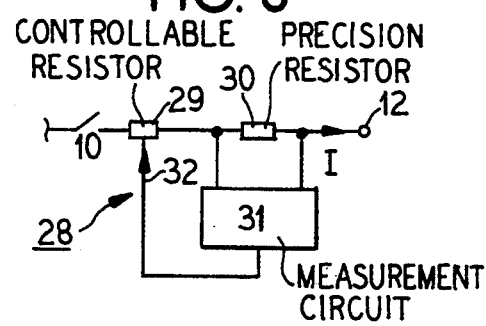
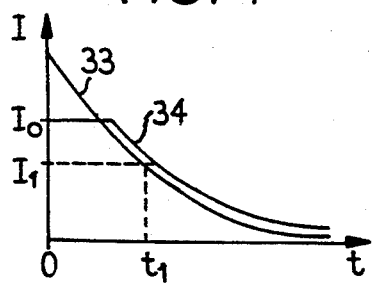
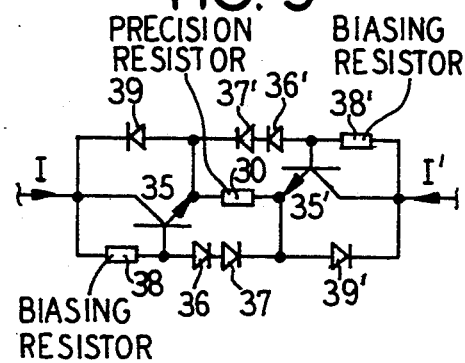
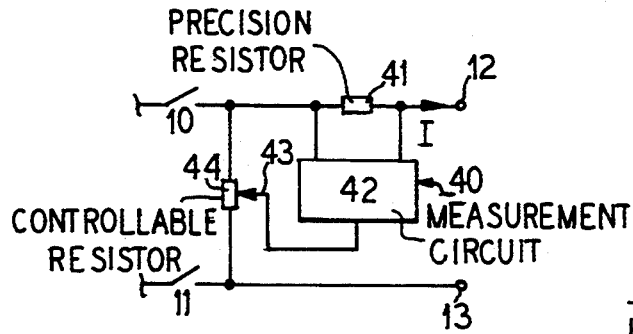
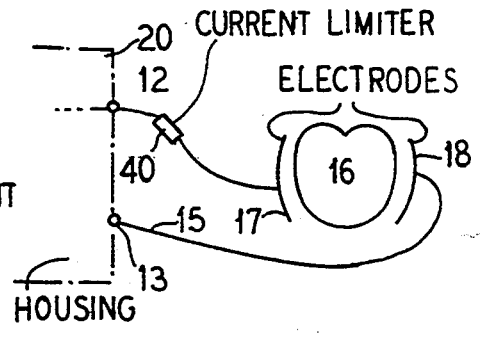

DEFIBRILLATOR WITH CURRENT LIMITER

This application is a continuation of Ser. No. 08/045,299, filed Apr. 12, 1993, now abandoned.

BACKGROUND OF THE INVENTION

1. Field of the Invention

The present invention is directed to a defibrillator having a charging capacitance that can be switched at both its sides for connection to a charging circuit and that can be connected via a switch means to at least two electrodes arranged in the region of the heart for defibrillating a heart.

2. Description of the Prior Art

A defibrillator of the type described above is disclosed in U.S. Pat. No. 4,800,883 is intended for implantation in the body of a patient. This known defibrillator contains a charging capacitance composed of two capacitors that are connected to a charging circuit for charging to a given voltage. The two capacitors are also connected to two electrodes placed at the heart of the patient, via a switch means composed of four switches arranged in bridge circuitry. For defibrillation of the heart, the charging capacitance is first charged to the given voltage and is subsequently connected to the electrodes at the heart via the switch means, so that the charging capacitance discharges with a discharge current via the heart tissue. The four switches of the switch means are alternately opened and closed in pairs, so that the discharge current through the heart tissue is subdivided into a plurality of successive sub-currents having alternating direction of the current.

A circuit is described in European Application 0 060 404 which limits the current through the paddles of an external defibrillator. This circuit, however, makes use of inductances for the current limitations which are too heavy and large for use in an implantable device.

The current through the heart tissue that produces defibrillation is dependent on the charging voltage of the charging capacitance and on the electrical resistance of the heart tissue between the electrodes. The current has its highest value at the beginning of the discharge of the charging capacitance and then exponentially decays. In order to obtain an effective defibrillation of the heart, the current through the heart tissue must exceed a specific minimum value over a specific duration. For this reason, the charging voltage for the charging capacitance is selected such that the current is adequately high at the beginning of the discharge event so that it does not drop below the minimum value until the expiration of the specific duration. The part of the current exceeding the minimum value is not only useless in view of an effective defibrillation but, moreover may cause damage to the heart tissue as a consequence of the high initial value. A further problem is that shorts can occur between the electrodes due to a fault or due to damage in the leads of the electrodes or given dislocation of the electrodes, so that the short-circuit current arising when triggering the discharge of the charging capacitor can cause damage to the patient and to the defibrillator. Such shorts can also occur during manufacture and during later handling of the defibrillator in conjunction with the implantation thereof, so that there is a risk to the person handling the defibrillator.

SUMMARY OF THE INVENTION

It is an object of the present invention to prevent the occurrence of successively high discharge currents in a defibrillator without the effectiveness of the defibrillation being thereby influenced.

This object is inventively achieved in accordance with the principles of the present invention in a defibrillator of the type initially cited, further having non-inductive means for limiting the current to a prescribed maximum value arranged in the current path from the charging capacitor to the electrodes. The discharge current of the charging capacitor, and thus the current to the heart tissue, are thereby limited to the prescribed maximum value during normal operation of the defibrillator, so that damage to the heart tissue is precluded. This current limitation is also effective in the event of a malfunction, for example a short between the electrodes, so that damage to the defibrillator is prevented.

In an embodiment of the means for current limitation that is especially simple in terms of design, and also is space-saving, this means is composed of a resistor element having a positive temperature characteristic (PTC resistor). Such a resistor element, that is usually composed of a semiconducting ceramic, increases its value of resistance given increasing temperature due to the current flowing through the resistor element, the current being limited as the result thereof.

Resistor elements consisting of semiconductive polymer have been known for some time, functioning as self-healing fuses in that they suddenly increase their value of resistance at a specific value of temperature that corresponds to a specific current and thus effect an interruption of the current until the temperature has dropped below the prescribed value. When only protection against potential shorts is desired in the defibrillator of the invention, then such a resistor element is particularly advantageous because of its fast response time.

In an alternative fashioning of the defibrillator of the invention, the means for current limitation comprises a low-impedance precision resistor arranged in the current path, a measurement circuit acquiring the voltage drop-off caused by the current in the precision resistor connected in parallel with the precision resistor, and the measurement circuit has its output side connected to the control input of a controllable resistor or switch. The controllable resistor or switch is either arranged in series with the precision resistor in the current path and is driven into a higher-impedance, or open, condition when the maximum value of the current is reached, or is arranged in a current branch parallel to the charging capacitor and is driven into a lower-impedance, or closed, condition when the maximum value of the current is reached. The current limitation thereby ensues independently of any and all temperature compensation events and is therefore especially fast and precise. Moreover, there is the possibility of setting different values for the maximum value of the current to be limited by varying the control behavior of the measurement circuit.

The current limitation provided according to the invention proves especially advantageous when the charging circuit, the charging capacitor and the switch means in the defibrillator are arranged in a housing implantable in the body of a patient. Since the electrode leads and electrodes are no longer accessible without further difficulty after an implantation of such a defibrillator, there is an especially great need for a current limitation in that case wherein the electrode line or electrodes change their position in the body of the patient and can thus cause shorts. The means for current limitation is thus preferably arranged in the housing, so that the current limitation ensues independently of the location of the electrode lines at which a short may possibly occur. It also possible, however, to arrange the means for current limitation in an electrode lead given a corresponding insulation of the electrode leads.

In order to also be able to retrofit conventional defibrillators without means for current limitation to provide them with non-inductive current limiting means in accordance with the invention, the means for current limitation of the invention is arranged in a plug part that is provided with terminal elements for connection of the housing of a conventional defibrillator, and is provided with further terminal elements for the connection of at least one of the electrodes.

DESCRIPTION OF THE DRAWINGS

FIG. 1 is a simplified block circuit diagram of a defibrillator having a PTC resistor for current limitation constructed in accordance with the principles of the present invention.

FIG. 2 shows an example of the arrangement Of the PTC resistor in a plug part connectable to the housing of the defibrillator.

FIG. 3 is a simplified block circuit diagram of an alternative fashioning of the means for current limitation having a controllable resistor controlled dependent on the current through a precision resistor.

FIG. 4 is a diagram showing the output current of the defibrillator with current limitation achieved with the invention and without current limitation.

FIG. 5 is an example of the circuit schematic for the means for current limitation of FIG. 3.

FIG. 6 is an alternative embodiment of the means for current limitation constructed in accordance with the principles of the present invention, having a controllable resistor that branches off the excess current part from the current to be limited.

FIG. 7 shows an embodiment wherein a current limiter is contained in one of the electrode leads.

DESCRIPTION OF THE PREFERRED EMBODIMENTS

The defibrillator of the invention shown in FIG. 1 in a block circuit diagram contains a voltage source 1 in the form of a battery that is connected to a charging circuit 2 for a charging capacitor 3. The charging circuit 2 generates a prescribed charging voltage at its output terminals 4 and 5 to which the charging capacitor 3 is charged when it is connected to the output terminals 4 and 5 at both of its sides 6 and 7 via two controllable switches 8 and 9. The two sides 6 and 7 of the charging capacitor 3 are also respectively connectable to two electrode terminals 12 and 13 via a controllable switch means composed of two further switches 10 and 11. Two electrodes 17 and 18 arranged in the region of the heart 16 of a patient are connected to the electrode terminals 12 and 13 via respective electrode lines 14 and 15. A resistor element 19 having a positive temperature characteristic (PTC) is arranged between the controllable switch 10 and the electrode terminal 12 in the current path from the charging capacitor 3 to the electrodes 17 and 18. The resistor element 19, which is composed of a semiconductive ceramic or of a semiconductive polymer, has a low value of resistance at a current below a prescribed maximum value. When the electrical current through the resistor element 19 reaches the prescribed maximum value, the value of resistance of the resistor element 19 markedly rises due to the rise in temperature of the resistor element 19 and thereby limits the current through the resistor element 19—or interrupts it in the case of the semiconductive polymer. It is thus assured that the discharge current of the discharge capacitor 3 is limited to the prescribed maximum value in the event of a short between the electrode lines 14 and 15 or between the electrodes 17 and 18.

The exemplary embodiment shown in FIG 1 shows only those parts of the defibrillator essential for an understanding of the invention. The circuit parts that are required for controlling the switches 8 through 11 as well as for controlling the charging circuit 2 for the purpose of setting the prescribed charging voltage for the charging capacitor 3 are not shown. Further, the charging capacitor 3 can be composed of a plurality of capacitors and the controllable switch means formed by switches 10 and 11 can alternatively be fashioned as a bridge circuit as in the defibrillator disclosed in the aforementioned U.S. Pat. No. 4,800,883, so that the discharge current of the charging capacitor 3 can flow through the heart 16 in opposite directions. As shown, the electrodes 17 and 18 can be fashioned as surface (or planar) electrodes or as catheter electrodes and can be arranged outside the heart 16 or in the heart 16. Further electrodes can also be provided, these being connected to the illustrated electrodes 17 and 18.

In the exemplary embodiment shown in FIG. 1, the battery 1, the charging circuit 2, the charging capacitor 3, the controllable switches 8 through 11 and the current-limiting resistor element 19 are accommodated in a housing 20 having a conventional size and shape implantation in the body of the patient.

FIG. 2 shows an alternative arrangement of a current-limiter 21 in a plug part 22 that has a terminal pin 23 for connecting the plug part 22 to the terminal part 24 of an implantable defibrillator 25 and which contains a jack 26 for connection of an electrode lead 37. There is thereby the possibility of retrofitting known defibrillators without current-limitation to provide such defibrillators with current limitation in accordance with the invention.

FIG. 3 shows an alternative embodiment of the means for current limitation 28, wherein a controllable current interrupter, such as a controllable resistor 29, in series with a low-impedance, precision resistor 30 is arranged in the current path from the charging capacitor to the electrodes-between the controllable switch 10 and the electrode connection 12 with reference to FIG. 1. The measuring circuit 31 has its measuring inputs arranged in parallel with the precision resistor 30 and has its output side connected to a control input 32 of the controllable resistor 29. The measurement circuit 31 acquires the voltage drop caused by the current I in the precision resistor 30 across its measuring inputs and controls the controllable resistor 29 in such a way that the resistor 29 is driven into a high-impedance condition when a prescribed maximum value $I_o$ of the current I is reached, so that the current I is limited to the maximum value $I_o$. A controllable switch may be used as the current interrupter instead of the controllable resistor 29, such a controllable switch effecting an interruption of the current flow whenever the current I reaches the maximum value $I_o$. The "open" state of the switch thus constitutes a "high impedance" state.

FIG. 4 illustrates the operation of the invention with reference to two current curves 33 and 34; the current curve references 33 occurs when the switches 10 and 11 are closed at time t=0 and the charging capacitor 3 discharges across the heart tissue 16 without any kind of current limitation. The current curve 33 has its highest value at the beginning of the discharge of the charging capacitor 3 and exponentially decays thereafter, with the minimum current for effective defibrillation of the heart 16, referenced $I_1$, being downwardly transgressed time $t_1$. As FIG. 4 shows, the initial value of the current curve 33 can lie considerably above the defibrillation threshold $I_o$, in which range damage to the heart tissue 16 may arise. With the means for current limitation 28 as shown in FIG. 3, by contrast, one obtains the current curve referenced 34 wherein the current I at the start of the discharge of the charging capacitor is limited to a non-injurious maximum value $I_o$ and, in addition, advantageously lies above the minimum value $I_1$ required for defibrillation beyond the time $t_1$.

FIG. 5 shows an exemplary embodiment of the means for current limitation 28 that is only schematically shown in FIG. 3. The controllable resistor 29 (i.e., controllable resistance) is thereby fashioned in the form of a transistor 35 having its emitter arranged in series with the precision resistor 30. Two diodes 36 and 37 lie in series between the base of the transistor 35 and the terminal of the precision resistor 30 distal from the emitter, these diodes 36 and 37 being supplied by a partial current branched off from the current I with a biasing resistor 38 between the collector and the base of the transistor 35. The current I is limited to the maximum value $I_o=(2U_D-U_{BE})/R$ in this way, whereby $U_D$ is the on-state voltage of one of the diodes 36 and 37, $U_{BE}$ is the base-emitter voltage of the transistor 35, and R is the value of resistance of the precision resistor 30. In order also to obtain a current limitation given a current I' flowing opposite the current I, a further transistor 35' having diodes 36' and 37' and a biasing resistor 38' are provided in a mirror-symmetric arrangement with reference to the precision resistor 30. Two further diodes 39 and 39' in anti-parallel arrangement relative to the collector-emitter paths of the transistors 35 and 35' conduct the current I' or I flowing opposite the conducting direction of the respective transistor 35 or 35'.

FIG. 6 shows an exemplary embodiment of the current-limiting means 40, wherein a controllable precision resistor 41 is arranged in the current path from the charging capacitor to the electrodes—between the controllable switch 10 and the electrode terminal with reference to FIG. 1. A measuring circuit 42 has its measuring input arranged in parallel with the precision resistor 41 and has its output side connected to the control input 43 of a controllable current interrupter, such as a controllable resistor 44, that is arranged between the junction of the switch 10 and the precision resistor 41, hand and the electrode terminal 13. The measurement circuit 42 acquires the voltage drop produced across the precision resistor 41 by the current I at its measuring inputs and controls the controllable resistor 44 such that the resistor 44 is driven into a low-impedance condition when a prescribed maximum value $I_o$ of the current I is reached, so that a sub-current of the discharge current from the charging capacitor 3 is diverted across the control resistor 44 and the current I across the heart tissue 16 is thus limited to the maximum value $I_o$. Again, a switch may be used instead of the controllable resistor 41, with the "closed" state of the switch representing a "low impedance" state.

As schematically shown in FIG. 7, the current limiter 40 (which may be the PTC resistor element 19 of FIG. 1, the controllable resistor 29 or 44 of FIGS. 3 and 6, respectively, or some or all of the components of FIG. 5) may be contained in one of the electrode lines (leads), such as line 14.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable defibrillator comprising:

a housing having a size and shape for implantation in a patient;

a capacitance contained in said housing;

charging circuit means contained in said housing for charging said capacitance;

switch means contained in said housing for discharging said capacitance for defibrillating a heart;

at least two electrodes each having a proximate end connected to said switch means and a distal end arrangeable in a region of said heart for in vivo delivery of said current to heart tissue, said capacitance and the distal end of one of said electrodes being electrically connected by a current path extending in said housing and in said one of said electrodes, along which said current flows from said capacitance to the distal end of said one of said electrodes, and non-inductive current limiting means disposed in vivo in said current path for limiting current supplied to said heart tissue to a predetermined maximum value and for otherwise permitting all of said current to flow in said current path.

2. An implantable defibrillator as claimed in claim 1, wherein said non-inductive current limiting means comprises a resistor element having a positive temperature characteristic.

3. An implantable defibrillator as claimed in claim 2 wherein said resistor element consists of a semiconductive polymer.

4. An implantable defibrillator as claimed in claim 1 wherein said non-inductive current limiting means comprises:

a low-impedance precision resistor connected in said current path;

a controllable current interrupter connected in said current path in series with said precision resistor and driveable into a high-impedance state by a control signal; and current measuring means, having inputs connected across said precision resistor, for measuring a voltage drop across said precision resistor caused by said current and for supplying said control signal to said controllable current interrupter when said predetermined maximum value of said current is reached.

5. An implantable defibrillator as claimed in claim 4 wherein said controllable current interrupter comprises a controllable resistor.

6. An implantable defibrillator as claimed in claim 4 wherein said controllable current interrupter comprises a controllable switch.

7. An implantable defibrillator as claimed in claim 1 wherein said non-inductive current limiting means comprises:
- a low-impedance precision resistor connected in said current path;
- a controllable current interrupter connected in parallel with said capacitance and driveable into a low-impedance state by a control signal; and
- measurement means, having inputs connected across said precision resistor, for measuring a voltage drop across said precision resistor caused by said current and for supplying said control signal to said controllable current interrupter when said predetermined maximum value of said current is reached.

8. An implantable defibrillator as claimed in claim 7 wherein said controllable current interrupter comprises a controllable resistor.

9. An implantable defibrillator as claimed in claim 7 wherein said controllable current interrupter comprises a controllable switch.

10. An implantable defibrillator as claimed in claim 1 wherein said non-inductive current limiting means is contained in said housing.

11. An implantable defibrillator as claimed in claim 1 wherein said non-inductive current limiting means is contained in said one of said electrodes outside of said housing.

12. An implantable defibrillator as claimed in claim 5 further comprising a plug element having a first terminal element for mechanical and electrical connection to said housing and a plurality of further terminal elements for respective electrical and mechanical connection to said electrodes, and wherein said non-inductive current limiting means is contained in said plug element.

* * * * *